(12) United States Patent
Brannen et al.

(10) Patent No.: US 12,071,401 B2
(45) Date of Patent: Aug. 27, 2024

(54) DIRECT CONVERSION OF ESTERS TO CARBOXYLATES

(71) Applicant: NIACET CORPORATION, Niagara Falls, NY (US)

(72) Inventors: Kelly Brannen, North Palm Beach, FL (US); David J. Harrigan, Lewiston, NY (US); Donal S. Tunks, Grand Island, NY (US); Stanley A. Sojka, Grand Island, NY (US)

(73) Assignee: NIACET CORPORATION, Niagara Falls, NY (US)

( * ) Notice: Subject to any disclaimer, the term of this patent is extended or adjusted under 35 U.S.C. 154(b) by 0 days.

(21) Appl. No.: 18/460,239

(22) Filed: Sep. 1, 2023

(65) Prior Publication Data

US 2023/0406806 A1 Dec. 21, 2023

Related U.S. Application Data

(63) Continuation of application No. 17/476,752, filed on Sep. 16, 2021, now abandoned.

(60) Provisional application No. 63/079,683, filed on Sep. 17, 2020.

(51) Int. Cl.
*C07C 51/41* (2006.01)
*C07C 51/47* (2006.01)

(52) U.S. Cl.
CPC ............ *C07C 51/412* (2013.01); *C07C 51/47* (2013.01)

(58) Field of Classification Search
CPC ....... C07C 51/412; C07C 51/47; C07C 53/10; C07C 53/122; C07C 53/124
See application file for complete search history.

(56) References Cited

U.S. PATENT DOCUMENTS

| | | | | |
|---|---|---|---|---|
| 2,033,909 A | * | 3/1936 | Cox | C07C 51/412 562/577 |
| 4,427,572 A | | 1/1984 | Akers et al. | |
| 4,700,000 A | * | 10/1987 | Merkel | C07C 51/412 562/606 |
| 5,783,714 A | | 7/1998 | Mckenna et al. | |
| 6,673,964 B1 | | 1/2004 | Uriarte et al. | |
| 2005/0049433 A1 | | 3/2005 | Fan et al. | |
| 2007/0169671 A1 | | 7/2007 | Johnston | |
| 2018/0370897 A1 | * | 12/2018 | Lalgudi | C07C 67/03 |

FOREIGN PATENT DOCUMENTS

| | | |
|---|---|---|
| CN | 101747174 A | 6/2010 |
| CN | 103113213 A | 5/2013 |
| CN | 104496790 A | 4/2015 |
| CN | 105566098 A | 5/2016 |
| CN | 106946687 A | 7/2017 |
| CN | 108077709 A | 5/2018 |
| CN | 106699802 B | 1/2019 |
| EP | 1072581 A2 | 1/2001 |
| JP | H0251504 | * 10/1990 |
| JP | 2009234968 A | 10/2009 |
| SK | 279966 | * 7/1996 |
| SK | 279966 B6 | 7/1996 |

OTHER PUBLICATIONS

Cavalli et al. (Atmospheric Oxidation Mechanism of Methyl Propionate, J. Phys. Chem. A, 104. pp. 11310-11317, Published 2000) (Year: 2000).*
SK279966 translated (Year: 1996).*
JPH0251504 translated (Year: 1990).*
NGS (Nitrogen Gas Sparging—South-Tek Systems pp. 1-6, Published Mar. 2016) (Year: 2016).*
Yolanda et al. (Kinetics of the CaO/Ca(OH)2 Hydration/Dehydration Reaction for Thermochemical Energy Storage Applications, Industrial and Engineering Chemistry Research, pp. 12594-12601) (Year: 2014).*
English Abstract of Cheng, J. et al., Huaxue Shijie, 35(5): 256-7 (1994).
English Abstract of Wang, S. et al., Zhengzhou Liangshi Xueyuan Xuebao, 19(1): 24-27 (1998).
Food Chemicals Codex 11, "Calcium Propionate," US Pharmacopeia, p. 221 (2018).
NGS (Nitrogen Gas Sparging 6 pages Published 2014) (Year: 2014).

* cited by examiner

*Primary Examiner* — Jafar F Parsa
*Assistant Examiner* — Blaine G Doletski
(74) *Attorney, Agent, or Firm* — Sughrue Mion, PLLC

(57) ABSTRACT

A calcium carboxylate is prepared by reacting water, calcium oxide, and a compound of formula (I):

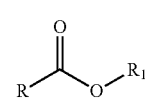

wherein R is a $C_1$-$C_3$ alkyl and $R_1$ is a $C_1$ or $C_2$ alkyl. The reaction solution is heated to remove an amount of a co-product from the reaction solution. The calcium carboxylate may be recovered in a solid form from the reaction solution.

18 Claims, 1 Drawing Sheet

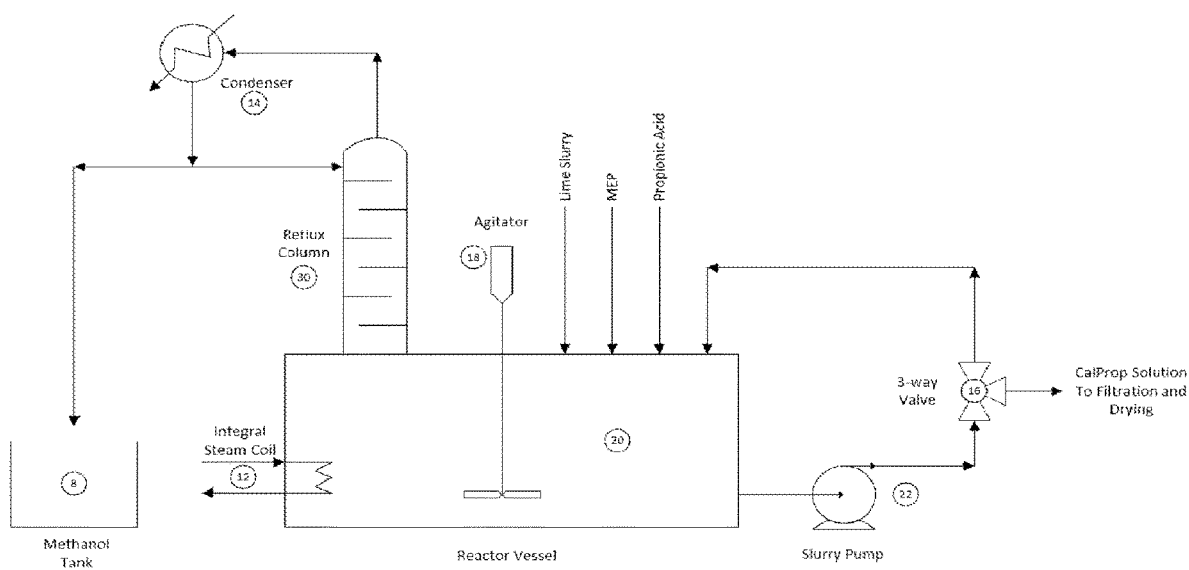

DIRECT CONVERSION OF ESTERS TO CARBOXYLATES

CROSS-REFERENCE TO RELATED APPLICATIONS

This application is a continuation of U.S. application Ser. No. 17/476,752, filed Sep. 16, 2021, which is based on and claims priority under 35 U.S.C § 119 from U.S. Provisional Application No. 63/079,683, filed Sep. 17, 2020, the contents of both are incorporated herein by reference in their respective entireties.

FIELD OF THE INVENTION

The present invention relates to processes for the production of a calcium carboxylate directly from an ester or anhydride.

BACKGROUND OF THE INVENTION

Calcium carboxylates are useful in the production of the corresponding carboxylic acids. Calcium carboxylates also have other beneficial applications. For example, calcium acetate is used as a thickening agent, such as in cake batters, puddings, and pie fillings, as buffers in controlling pH of food during various stages of processing as well as in the finished product, as a preservative to prevent microbial growth, and as a calcium supplement in pet products. In addition, calcium propionate is used on a large scale as a preservative in the foodstuffs sector, particularly in baked goods, and as a preservative and nutritional supplement in animal feeds.

There is recent interest in short-chain fatty acids because of their beneficial effects on gut microbiome. Moreover, acetates, propionates, butyrates, and lactates, for example, have shown antimicrobial properties which have been commercially useful.

Calcium carboxylates are typically prepared by the conventional methods for synthesizing carboxylic acid salts, for example by reacting a carbonate, hydroxide, or oxide with a concentrated or dilute carboxylic acid. Calcium propionate, for instance, is typically produced from propionic acid and calcium.

Given the many and wide variety of uses for calcium carboxylates, there is a need for improved processes for their production. Particularly, there is a need for improved processes that can be performed quickly, result in high yields, consume less energy, and/or that generate minimal waste.

SUMMARY OF THE INVENTION

The invention is directed to methods of converting esters to calcium carboxylates.

Accordingly, one embodiment is a method of reacting water, calcium oxide, and a compound of formula (I):

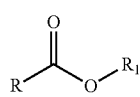

(I)

wherein R is a $C_1$-$C_3$ alkyl and $R_1$ is a $C_1$ or $C_2$ alkyl, to obtain a reaction solution and heating the reaction solution to remove an amount of a co-product from the reaction solution. Further, the calcium carboxylate may be recovered in solid form from the reaction solution.

Another embodiment is a method for producing calcium propionate comprising reacting water and calcium oxide to obtain a slurry; reacting the slurry with methyl propionate, wherein the calcium oxide is reacted in a molar excess compared to the methyl propionate, to obtain a reaction solution; heating the reaction solution to remove an amount of methanol from the reaction solution; neutralizing the reaction solution to a pH of from 7.0 to 9.5 by adding a sufficient quantity of propionic acid; and filtering the reaction solution. Further, the calcium propionate may be recovered in solid form from the filtered reaction solution.

The invention is further directed to methods of converting anhydrides to calcium carboxylates.

Additional objects and advantages of the invention will be set forth in part in the description which follows, and in part will be obvious form the description, or may be learned by practice of the invention. The objects and advantages of the invention will be realized and attained by means of the elements and combinations particularly pointed out in the appended claims.

It is to be understood that the foregoing general description and the following detailed description are exemplary and explanatory only and are not restrictive of the invention, as claimed.

BRIEF DESCRIPTION OF THE DRAWINGS

The FIGURE is an apparatus for the conversion of methyl propionate to calcium propionate. The reference numbers in the FIGURE correspond to a methanol tank 8; an integral steam coil 12; a condenser 14; a 3-way valve 16; an agitator 18; a reactor vessel 20; a slurry pump 22; and a reflux column 30.

DETAILED DESCRIPTION OF THE INVENTION

While it was anticipated that the insolubility of carboxylate salts containing the $Ca^{+2}$ cation would be problematic, the inventors discovered a process that directly converts esters of formula (I) to calcium carboxylates according to the following reaction:

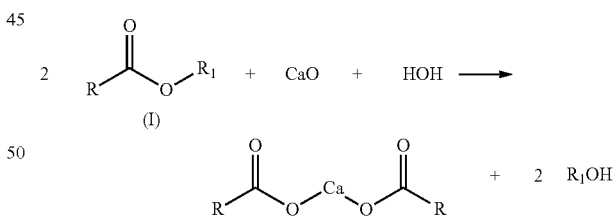

wherein R and $R_1$ are, independently, selected from H, Ph, Ar, a substituted $C_1$-$C_{60}$ alkyl, and an unsubstituted $C_1$-$C_{60}$ alkyl.

The inventors also discovered a process that directly converts anhydrides of formula (II) to calcium carboxylates according to the following reaction:

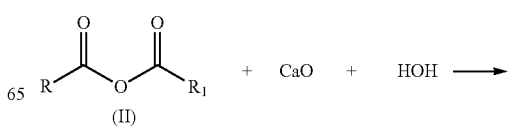

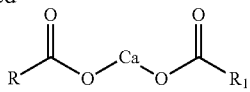

wherein R and $R_1$ are, independently, selected from H, Ph, Ar, a substituted $C_1$-$C_{60}$ alkyl, and an unsubstituted $C_1$-$C_{60}$ alkyl.

The $C_1$-$C_{60}$ alkyl may be substituted with at least one substituent selected from the group consisting of: F, Cl, Br, I, At, O, S, S(O), $SO_2$, N, P, P(O), Si, Si(O), B, Al, and combinations thereof. Suitably, Ar is a $C_6$ or $C_{12}$ aryl or heteroaryl optionally substituted group where the heteroatom may be O or N and the substituent may be selected from the group consisting of H, F, Cl, Br, I, At, $SO_2$, $NH_2$, $NHR$, $NR_2$ and combinations thereof, where R is as defined herein. The number of such substituents to be substituted on the $C_1$-$C_{60}$ alkyl may be 1, 2, 3 or 4.

In another embodiment, the $C_1$-$C_{60}$ alkyl is substituted with at least one Cl substituent. In yet a further embodiment, the $C_1$-$C_{60}$ alkyl is substituted with two Cl substituents.

In one embodiment, R and $R_1$ are, independently, selected from the group consisting of H and an unsubstituted $C_1$-$C_{60}$ alkyl. In another embodiment, R and $R_1$ are, independently, selected from the group consisting of an unsubstituted $C_1$-$C_8$ alkyl. In yet another embodiment, R and $R_1$ are, independently, selected from the group consisting of an unsubstituted $C_1$-$C_6$ alkyl. In yet another embodiment, R and $R_1$ are, independently, selected from the group consisting of an unsubstituted $C_1$-$C_4$ alkyl.

R and $R_1$ may each be an unsubstituted $C_1$ alkyl. R and $R_1$ may each be an unsubstituted $C_2$ alkyl. In another embodiment, R is an unsubstituted $C_2$ alkyl and $R_1$ is an unsubstituted $C_1$ alkyl. In yet another embodiment, R is an unsubstituted $C_3$ alkyl and $R_1$ is an unsubstituted $C_1$ alkyl.

The compound of formula (I) and the compound of formula (II) may comprise fewer than ten, eight, six, five, or four carbon atoms. In one embodiment, the compound of formula (I) and the compound of formula (II) comprise fewer than six carbon atoms.

The term "alkyl", unless otherwise stated, a straight or branched chain, acyclic or cyclic hydrocarbon radical, or combination thereof, which may be fully saturated, mono- or polyunsaturated and can include di- and multi-valent radicals, having the number of carbon atoms designated (e.g., $C_{1-10}$ means one to ten carbons) and may be substituted or unsubstituted. Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers.

The compound of formula (I) may be methyl acetate, ethyl propionate, methyl propionate, or methyl butanoate. In one embodiment, the compound of formula (I) is methyl propionate.

The compound of formula (II) may be acetic anhydride, propionic anhydride, butanoic anhydride, or acetic propionic anhydride. In one embodiment, the compound of formula (II) is acetic anhydride.

The amount of calcium oxide employed in the conversion of a compound of formula (I) can be expressed as a molar ratio of calcium oxide to the compound of formula (I). Broadly, a molar excess of calcium oxide compared to the compound of formula (I) may be employed. The molar ratio of calcium oxide to the compound of formula (I) may be from 0.5:1 to 0.75:1. A stoichiometric excess of the calcium oxide compared to the compound of formula (I), i.e. a molar ratio greater than 0.5:1 will result in an excess of the calcium oxide. For example, a molar ratio of 0.75:1 corresponds to a molar excess of 50% The molar ratio of calcium oxide to the compound of formula may be from 0.5:1 to 0.6:1 (an excess of calcium oxide up to a 20% molar excess). The molar ratio of calcium oxide to the compound of formula may be about 0.505:1 to about 0.55:1 (a molar excess of 1% to 10%).

The amount of calcium oxide employed in the conversion of a compound of formula (II) can be expressed as a molar ratio of calcium oxide to the compound of formula (II). Broadly, a molar excess of calcium oxide compared to the compound of formula (II) may be employed. The molar ratio of calcium oxide to the compound of formula (II) may be from 1:1 to 1.5:1. A stoichiometric excess of the calcium oxide compared to the compound of formula (II), i.e. a molar ratio greater than 1:1 will result in an excess of the calcium oxide. For example, a molar ratio of 1.5:1 corresponds to a molar excess of 50% The molar ratio of calcium oxide to the compound of formula (U) may be from 1:1 to 1.2:1 (an excess of calcium oxide up to a 20% molar excess). The molar ratio of calcium oxide to the compound of formula (II) may be about 1.01:1 to about 1.1:1 (a molar excess of 1% to 10%).

The amount of water employed in the process is the amount necessary to form a slurry; one of ordinary skill in the art is capable of adjusting the amount of water such that the amount is not too large to destroy the volumetric throughput of a reaction vessel and not too small such that the slurry would be immovable, i.e. incapable of being mixed and/or pumped. In one embodiment, the amount of calcium hydroxide formed from the reaction of water and calcium oxide is from 8% to 10% (w/w). In another embodiment, the amount of calcium hydroxide formed from the reaction of water and calcium oxide is from 10% to 30% (w/w). In still another embodiment, the amount of calcium hydroxide formed from the reaction of water and calcium oxide is from 30% to 60% (w/w).

The calcium oxide, water, and compound of formula (I) or (II) may be reacted in any order and in one or more reaction vessels. For instance, the calcium oxide and water may be reacted in a first reaction vessel, followed by reaction with the compound of formula (I) or (II) in a second reaction vessel. In another embodiment, the reaction may take place in a single reaction vessel. For instance, water may be added to the single reaction vessel, followed by the calcium oxide, followed by the compound of formula (I) or (II). Alternatively, calcium oxide may be added to the single reaction vessel, followed by the water, followed by the compound of formula (I) or (II).

One or more of the calcium oxide, water, and compound of formula (I) or (II) may be added over a period of time instead of in a single bolus. For instance, the compound of formula (I) or (II) may be added to a reaction vessel over a period of up to three hours. In one embodiment, the compound of formula (I) or (II) is added to a reaction vessel over a period of from 30 to 120 minutes. In yet another embodiment, the compound of formula (I) or (II) is added to a reaction vessel over a period of 30 minutes, 45 minutes, 60 minutes, 90 minutes, or 120 minutes.

The process of the invention can generally be conducted at a temperature sufficient to allow the reaction to proceed. For instance, the temperature of the reaction may be from 50° C. to 100° C. Temperature of the reaction may be maintained, if necessary, by conventional techniques, such as by employing a heating coil or mantle. The reaction time will be the time suitable to obtain the desired conversion of the compound of formula (I) or (II) into calcium carboxylate. Generally, the reaction time will vary depending on process parameters including the reaction temperature and the compound of formula (I) or (II) used. For instance, after addition of the reactants is complete, the reaction may be allowed to proceed for from 2 to 4 hours, or from 2 to 8 hours, or from 2 to 12 hours. The process of the invention can be conducted as a batch, semi-batch, or continuous process depending on the scale of the process and capital investment required.

After completion of the reaction, whereby the reaction solution comprising the calcium carboxylate is obtained, the process further comprises removal of an amount of one or more co-products. The co-product may be, for instance, methanol or ethanol. The co-product may also be propanol or butanol.

In one embodiment, an amount of a co-product can be removed by heating the reaction solution to distill the co-product overhead. The temperature that the reaction solution is heated to will be any suitable temperature effective to remove the desired amount of co-product and will be readily apparent to those of ordinary skill in the an. The temperature may be, for instance, from 70° C. to 100° C., or from 70° C. to 150° C.

The time cycle for distillation can be set depending on the distillation conditions and the desired level of residual co-product in the calcium carboxylate product, and will be readily apparent to those of ordinary skill in the art. In one embodiment, nitrogen gas may be introduced below the liquid level of the reaction solution to aid in the distillation process. The distilled co-product may be sufficiently pure to be reclaimed and reused. It should be understood that it may not be possible to remove all amounts of a co-product from the reaction solution and that trace amounts of a co-product may therefore still exist in the reaction solution as an impurity. In one embodiment, substantially all of a co-product is removed from the reaction solution. In some embodiments, the amount of a co-product, such as methanol, is less than 1%, or 0.1%, or 0.01%, or 0.001%, or even undetectable relative to the calcium carboxylate in the reaction solution following distillation.

After completion of the distillation, it may be necessary to adjust the concentration of the calcium carboxylate in the reaction solution depending on the amount of water that has been removed during the distillation. Concentration adjustment may be needed, for instance, to ensure that all of the calcium carboxylate is in solution and/or to adjust the concentration of the calcium carboxylate if the final product is to be a solution. Concentration adjustment may be effected by, for example, adding additional water or other diluent to the reaction solution. In one embodiment, the concentration of the calcium carboxylate is adjusted to from 23% to 28% (w/w) by adding water. The concentration of the calcium carboxylate may be adjusted to, for instance, 25% or 26% (w/w) by adding water.

The reaction solution may be optionally neutralized and may also be optionally filtered. In other words, the reaction solution may only be neutralized, only be filtered, may be both neutralized and filtered, or may not be neutralized or filtered. The neutralization (pH adjustment) and filtration, if both performed, can be conducted in any order.

By way of example, the reaction solution may be filtered using conventional equipment and techniques after the distillation to remove excess insoluble calcium oxide, as well as any other impurities that may be adsorbed onto the particle surfaces, as well as any other insoluble materials present in the reactants used, such as sand, gravel, pebbles, carbonaceous material, polymers formed during the reaction, etc. Following the filtration, the pH may be adjusted with carboxylic acid corresponding to the calcium carboxylate to neutralize soluble calcium compound (forming additional calcium carboxylate) and reach the desired pH for the product. The pH may be adjusted to, for instance, from 7.0 to 9.5, from 7.0 to 8.0, or 7.5, or 10.0.

In another embodiment, neutralization with carboxylic acid corresponding to the calcium carboxylate to neutralize excess calcium compound present is performed. Filtration of the neutralized reaction solution is then conducted to remove remaining insolubles.

In yet another embodiment, no filtration is conducted. The reaction solution resulting from the distillation and optional concentration adjustment is neutralized with carboxylic acid corresponding to the calcium carboxylate to neutralize excess calcium oxide present.

Once any filtration and neutralization operations are conducted, the reaction solution may be subjected to further processing that is dependent on the form of the final product desired, for instance, a solution product or a solid product. For a solution product, the calcium carboxylate product optionally has the concentration adjusted by, for example, adding water or calcium carboxylate, and may have one or more additional filtrations using, for example, a polishing filter or equivalent separation device.

For a solid product, the calcium carboxylate product may be recovered and dried. Recovery and drying can be done utilizing any conventional process known to one of ordinary skill in the art. For example, the solution may be dried directly to a powder using a spray dryer or by spraying onto dry particles in a fluid bed dryer. In another embodiment, the calcium carboxylate product may be crystallized by water evaporation, collection on a filter or centrifuge, and final drying in any conventional solids dryer used to dry wet solids. In yet another embodiment, the calcium carboxylate solution may be processed through an agglomerator to make a granular product.

The purity of the solid calcium carboxylate may be determined according to standard Ca-EDTA titration as set forth in FCC 11 ("Calcium Propionate", Food Chemicals Codex 11, page 221, US Pharmacopeia, 2018). The purity of the solid calcium carboxylate may be, for instance, greater than 95.0%, greater than 98.0%, greater than 98.5%, greater than 99.0%, or greater than 99.5%, or greater than 99.9%.

EXAMPLES

The following examples are not meant to be limiting and represent certain embodiments of the present invention.

Example 1

Conversion of Methyl Acetate to Calcium Acetate

To a three-necked round bottom flask placed in a heating mantle and equipped with a mechanical stirrer, temperature-measuring thermocouple, and pressure-equalizing dropping funnel, was added 15.2 g (0.26 mole) of lime (95%; Specialty Minerals, Inc), followed by enough city water (159.9 g) to make a mixable slurry. The temperature of the slurry did not exceed 45° C. To this stirred slurry was dropwise added 40.7 g (0.55 mole) of methyl acetate (96.4%; Sekisui) over a period of 1.5 hr. After this addition was complete, the reaction solution was kept at 60° for 2 hr, and then the temperature was raised to 70° C. to distill volatile components into a receiver. A total of 26.5 g of distillate was collected over a period of 2 hr. Analysis of this distillate gave 11.8 g of water by Karl Fischer titration. The volatile organic constituents of the distillate were analyzed by gas chromatography to give 11.6 g of methanol (70% recovery), and 3.1 g of unreacted methyl acetate. The remaining contents of the round bottom flask had a pH of 6.7. Upon cooling, solids were precipitated, removed by filtration, and dried in an oven to give 37.9 g of calcium acetate (98.3% yield based on 92% conversion) as a white solid. Analysis by standard Ca-EDTA titration gave a purity of 99.8%.

Example 2

Conversion of Methyl Propionate to Calcium Propionate

To a three-necked round bottom flask placed in a heating mantle and equipped with a mechanical stirrer, temperature-measuring thermocouple, and pressure-equalizing dropping funnel, was charged 1600 g of city water followed by 127.7 g (2.28 mole) of lime (95%; Specialty Minerals, Inc) added in 6 min. To this stirred slurry was dropwise added 399 g (4.53 mole) of methyl propionate (99.95%; Lucite) over a period of 0.75 hr. After this addition was complete, the resultant reaction solution was kept at 60° for 2 hr and had a pH of 12.2. The pH was adjusted to 7.2 by addition of 38.8 g of propionic acid. The temperature of the reaction solution was raised to 95° C. to distill volatile components into a receiver. A total of 575.9 g of distillate was collected over a period of 6 hr. Analysis of this distillate gave 426.4 g of water by Karl Fischer titration. The volatile organic constituents of the distillate were analyzed by gas chromatography to give 149.5 g of methanol (103% recovery). The removal of the water by distillation was calculated to ensure that the remaining contents of the round bottom flask was a 26% aqueous solution of calcium propionate. This solution was filtered through diatomaceous earth. Upon cooling, solids were precipitated, removed by filtration, and dried in an oven to give 404.3 g of calcium propionate (95.9% yield) as a white solid. Analysis by standard Ca-EDTA titration gave a purity of 99.8%.

Example 3

Conversion of Ethyl Propionate to Calcium Propionate

To a three-necked round bottom flask placed in a heating mantle and equipped with a mechanical stirrer, temperature-measuring thermocouple, and pressure-equalizing dropping funnel, was added 12.8 g (0.2 mole) of lime (95%; Specialty Minerals, Inc), followed by enough city water (160.1 g) to make a mixable slurry. The temperature of the slurry did not exceed 45° C. To this stirred slurry was dropwise added 39.7 g (0.39 mole) of ethyl propionate (99%; Aldrich) over a period of 2 hr. After this addition was complete, the reaction solution was kept at 85° for 2 hr, and then the temperature was raised to 95° C. to distill volatile components into a receiver. A total of 52.3 g of distillate was collected over a period of 4 hr. Analysis of this distillate gave 35.3 g of water by Karl Fischer titration. The volatile organic constituents of the distillate were analyzed by gas chromatography to give 17 g of ethanol (95% recovery). No unreacted ethyl propionate was detected. Solids were removed from the round bottom flask by filtration and dried in an oven to give 30.4 g of essentially pure calcium propionate (84% yield) as a white solid.

Example 4

Conversion of Methyl Butanoate to Calcium Butanoate

To a three-necked round bottom flask placed in a heating mantle and equipped with a mechanical stirrer, temperature-measuring thermocouple, and pressure-equalizing dropping funnel, was added 12.7 g (0.2 mole) of lime (95%; Specialty Minerals, Inc), followed by enough city water (160.1 g) to make a mixable slurry. The temperature of the slurry did not exceed 45° C. To this stirred slurry was dropwise added 40 g (0.39 mole) of methyl butanoate (99%; Aldrich) over a period of 2 hr. After this addition was complete, the reaction solution was kept at 85° for 2 hr, and then the temperature was raised to 100° C. to distill volatile components into a receiver, A total of 36.8 g of distillate was collected over a period of Shr. Analysis of this distillate gave 23.5 g of water by Karl Fischer titration. The volatile organic constituents of the distillate were analyzed by gas chromatography to give 13.3 g of methanol (105% recovery). No unreacted methyl butanoate was detected. Solids were removed from the round bottom flask by filtration and dried in an oven to give 34.3 g of essentially pure calcium butanoate (94% yield) as a white solid.

Example 5

Conversion of Methyl Propionate to Calcium Propionate at Larger Scale

A lime slurry was prepared in a 55 gallon polypropylene tank fitted with an agitator by the addition of 12.8 kg of lime (95%; Specialty Minerals, Inc) into 131.9 kg of city water. This mixed slurry was pumped into a jacketed 50 gallon glass-lined steel reactor fitted with an agitator and condenser. To this reactor was then added 36.9 kg of methyl propionate (99.95%; Lucite) over a period of 0.75 hr. After this addition was complete, the reaction solution was kept at 65° C. for 1 hr. The temperature of the reaction solution did not exceed 65° C., and the final pH was adjusted from 11.3 to 7.8 by the addition of 0.9 kg of propionic acid. Nitrogen gas was introduced below the liquid level at a rate of 50 SCFH as the temperature was increased to 100° C. to distill off volatile components through the condenser and into a receiving vessel. After 6 hr of distillation, a total of 111.5 kg of distillate was collected and was analyzed as 96.4 kg of water, 13.4 kg of methanol (100% recovery), and 1.7 kg of unreacted methyl propionate. The removal of volatiles by distillation was calculated to ensure that the remaining contents of the reactor was a 25% aqueous solution of calcium propionate. This solution was filtered through diatomaceous earth. The solution was found to contain 38.8 kg of calcium propionate (99.5% yield) of 99.8% purity as determined by standard Ca-EDTA titration.

Example 6

Conversion of Acetic Anhydride to Calcium Acetate

To a three-necked round bottom flask placed in a heating mantle and equipped with a mechanical stirrer, temperature-measuring thermocouple, and pressure-equalizing dropping funnel, was added 15 g (0.25 mole) of lime (95%; Specialty Minerals, Inc), followed by enough city water (159.9 g) to make a mixable slurry. The temperature of the slurry did not exceed 65° C. To this stirred slurry was dropwise added 24.9 g (0.24 mole) of acetic anhydride (99%, Fisher) over a period of 2 hr. After this addition was complete, the reaction solution was kept at 70° C. for 4 hr. After this time, the pH of the final reaction solution was 12 and enough acetic acid was added to reduce the pH to 7.0. Analysis of the reaction solution by HPLC showed it to be an aqueous solution of essentially pure calcium acetate. The water was removed by evaporation to give 38.1 g of dry calcium acetate (98.8% yield) as an essentially pure white solid.

Example 7

Conversion System

The reactor system of this example is shown in the FIGURE. The system comprises a 50 gallon reaction vessel 20. Water and calcium oxide are reacted in a separate vessel (not pictured) and the slurry is added to the reaction vessel 20. Slurry pump 22 and 3-way valve 16 allow for the slurry to be recirculated through and recycled back to the reaction vessel 20 to ensure complete slurry formation. Methyl propionate (MEP) is fed into reaction vessel 20. The contents of the reaction vessel 20 are mixed using agitator 18. Propionic acid is added to the reaction vessel 20 in order to neutralize any remaining calcium hydroxide.

The reactor contents are heated using an integral steam coil 12. Water and methanol vapor generated when the contents in reaction vessel 20 are heated can be condensed at the top of a reflux column 30 and returned from condenser 14 to a methanol tank 8. The methanol and water may be recycled to the next consecutive batch. Once methanol has been removed, the calcium propionate solution is transferred by slurry pump 22 to a drum filter. The 3-way valve 16 can be turned to pump the reactor contents out of the reaction vessel 20 to the plant instead of being recycled to the reaction vessel 20.

The invention is also described in the following numbered clauses:

1. A process for producing calcium propionate comprising:
   a. reacting water and calcium oxide to obtain a slurry;
   b. reacting the slurry with methyl propionate, wherein the calcium oxide is reacted in a molar excess compared to the methyl propionate, to obtain a reaction solution;
   c. heating the reaction solution to remove an amount of methanol from the reaction solution;
   d. neutralizing the reaction solution to a pH of from 7.0 to 9.5 by adding a sufficient quantity of propionic acid; and
   e. filtering the reaction solution.

2. The process according to clause 1, further comprising adding nitrogen gas to the reaction solution during heating of the reaction solution.

3. The process according to clause 1, further comprising recovering the calcium propionate in a solid form from the filtered reaction solution.

4. The process according to clause 3, wherein the solid calcium propionate has a level of purity of 98.5% or greater, as measured by Ca-EDTA titration.

5. The process according to clause 1, wherein the pH is from 7.0 to 8.0.

6 The process according to clause 1, wherein the filtered reaction solution contains from 23% to 28% (w/w) calcium propionate.

7, A process for producing a calcium carboxylate comprising:
   a. reacting water, calcium oxide, and a compound of formula (I):

wherein
   R is a $C_1$-$C_3$ alkyl and
   $R_1$ is a $C_1$ or $C_2$ alkyl
   to obtain a reaction solution;
   b. heating the reaction solution to remove an amount of a co-product from the reaction solution; and
   c. filtering the reaction solution.

8. The process according to clause 7, wherein the calcium oxide is reacted in a molar excess compared to the compound of formula (I).

9. The process according to clause 7, wherein the compound of formula (I) is methyl propionate.

10, The process according to clause 7, wherein the compound of formula (I) is ethyl propionate, methyl butanoate, or methyl acetate.

11. The process according to clause 7, further comprising adding nitrogen gas to the reaction solution during heating of the reaction solution.

12. The process according to clause 7, further comprising recovering the calcium carboxylate in a solid form from the filtered reaction solution.

13. The process according to clause 12, wherein the solid calcium carboxylate has a level of purity of 98.5% or greater, as measured by Ca-EDTA titration.

14. The process according to clause 7, further comprising neutralizing the reaction solution to a pH1 of from 7.0 to 9.5 by adding a sufficient quantity of an acid.

15. The process according to clause 14, wherein the pH is from 7.0 to 8.0.

16. The process according to clause 7, wherein the filtered reaction solution contains from 23% to 28% (w/w) calcium carboxylate.

17. The process according to clause 7, wherein the compound of formula (I) has fewer than six carbon atoms.

18. A process for producing a calcium carboxylate comprising:
   a. reacting water, calcium oxide, and a compound of formula (I):

wherein
   R is a $C_1$-$C_3$ alkyl and
   $R_1$ is a $C_1$ or $C_2$ alkyl,
   to obtain a reaction solution; and
   b. heating the reaction solution to remove an amount of a co-product from the reaction solution.

19. The process according to clause 18, wherein the compound of formula (I) is methyl propionate.

20. The process according to clause 18, further comprising recovering the calcium carboxylate in a solid form from the reaction solution after heating.

We claim:

1. A process for producing calcium propionate, the process comprising:
   a. reacting water and calcium oxide to obtain a slurry;
   b. reacting the slurry with methyl propionate, wherein the calcium oxide is reacted in a molar excess compared to the methyl propionate, to obtain a reaction solution;
   c. heating the reaction solution to remove an amount of methanol from the reaction solution;
   d. neutralizing the reaction solution to a pH of from 7.0 to 9.5 by adding propionic acid;
   e. filtering the reaction solution; and
   f. recovering the calcium propionate in a solid form from the filtered reaction solution,
   wherein the solid calcium propionate has a level of purity of 95.0% or greater.

2. The process according to claim 1, further comprising adding nitrogen gas to the reaction solution during heating of the reaction solution.

3. The process according to claim 1, wherein the level of purity of the solid calcium propionate is 98.5% or greater.

4. The process according to claim 1, wherein the pH is from 7.0 to 8.0.

5. The process according to claim 1, wherein the filtered reaction solution contains from 23% to 28% (w/w) calcium propionate.

6. The process according to claim 1, wherein step b. is conducted at a temperature of from 50° C. to 100° C.

7. A process for producing a calcium carboxylate, the process comprising:
   a. reacting water, calcium oxide, and a compound of formula (I):

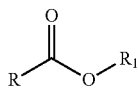
(I)

wherein:
   R is a $C_1$-$C_3$ alkyl and
   $R_1$ is a $C_1$ or $C_2$ alkyl,
to obtain a reaction solution;
   b. heating the reaction solution to remove an amount of a co-product from the reaction solution;
   c. filtering the reaction solution; and
   d. recovering the calcium carboxylate in a solid form from the filtered reaction solution,
   wherein the solid calcium carboxylate has a level of purity of 95.0% or greater.

8. The process according to claim 7, wherein the compound of formula (I) has fewer than six carbon atoms.

9. The process according to claim 7, wherein the compound of formula (I) is methyl propionate.

10. The process according to claim 7, wherein the compound of formula (I) is ethyl propionate, methyl butanoate, or methyl acetate.

11. The process according to claim 7, further comprising adding nitrogen gas to the reaction solution during heating of the reaction solution.

12. The process according to claim 7, wherein the level of purity of the solid calcium carboxylate is 98.5% or greater.

13. The process according to claim 7, further comprising neutralizing the reaction solution to a pH of from 7.0 to 9.5 by adding an acid.

14. The process according to claim 13, wherein the pH is from 7.0 to 8.0.

15. The process according to claim 7, wherein the filtered reaction solution contains from 23% to 28% (w/w) calcium carboxylate.

16. The process according to claim 7, wherein step a. is conducted at a temperature of from 50° C. to 100° C.

17. The process according to claim 7, wherein in the reacting step a, a molar ratio of the calcium oxide to the compound of formula (I) is from 0.505:1 to 0.75:1.

18. The process according to claim 1, wherein in the reacting step b, a molar ratio of the calcium oxide to the methyl propionate is from 0.505:1 to 0.75:1.

* * * * *